United States Patent [19]
Williams

[11] Patent Number: 5,061,803
[45] Date of Patent: Oct. 29, 1991

[54] PROCESS FOR MAKING 17-BETA ALKANOYL 3-OXO-4-AZA-5-α-ANDROST-1-ENES

[75] Inventor: John M. Williams, Somerset, N.J.

[73] Assignee: Merck & Co., Inc., Rahway, N.J.

[21] Appl. No.: 587,299

[22] Filed: Sep. 24, 1990

[51] Int. Cl.$^5$ .................... C07J 73/00; A61K 31/58
[52] U.S. Cl. ..................................... 546/77; 514/859
[58] Field of Search ................. 546/77; 514/284, 859

[56] References Cited

U.S. PATENT DOCUMENTS

| | | | |
|---|---|---|---|
| 4,220,775 | 2/1980 | Rasmusson et al. | 546/77 |
| 4,377,584 | 3/1983 | Rasmusson et al. | 424/258 |
| 4,760,071 | 7/1988 | Rasmusson et al. | 514/289 |
| 4,859,681 | 8/1989 | Rasmusson et al. | 546/77 |

FOREIGN PATENT DOCUMENTS 0155096 9/1985 European Pat. Off. .
0271219 6/1988 European Pat. Off. .

OTHER PUBLICATIONS

Advanced Organic Chemistry by Jerry March p. 434, John Wiley & Sons NY.
Synthesis, Nov. 1980, pp. 878–890.
Helv. Chim. Acta, vol. 69 (1986), pp. 228–235.
J. Med. Chem., vol. 29, No. 11, pp. 2298–2315 by Rasmusson et al.
"Protective Groups on Organic Synthesis" by Theodora W. Greene, 1981, Wiley, New York, pp. 40–41.

*Primary Examiner*—Mukund J. Shah
*Assistant Examiner*—Y. N. Gupta
*Attorney, Agent, or Firm*—Salvatore C. Mitri; Charles M. Caruso

[57] ABSTRACT

Disclosed is a new process for making 17-beta branched alkanoyl-3-oxo-4-aza-5-α-androst-1-enes, agents for treating benign prostatic hypertrophy (BPH), by reacting methyl 3-oxo-4-aza-5-α-androst-1-ene-17-beta carboxylate with isobutylmagnesium bromide in the novel presence of the hexamethyldisilazane (HMDS). Use of the HMDS results in higher yield and less by-products as opposed to the standard Grignard reaction in the absence of HMDS.

5 Claims, No Drawings

PROCESS FOR MAKING 17-BETA ALKANOYL 3-OXO-4-AZA-5-α-ANDROST-1-ENES

BACKGROUND OF THE INVENTION

17-Beta-keto-3-oxo-4-aza-5-α-androst-1-ene steroids are known in the art as benign prostatic hypertrophy (BPH) agents. See European Publication No. 0 155 096 and U.S. Pat. Nos. 4,220,775 and 4,377,584, all assigned to Merck & Co., Inc. Synthetic routes for their preparation are also described in *Synthesis*, November 1980, pp. 878–890 and *Helv. Chim. Acta*, Vol. 69 (1986), pp. 228–235.

General routes for synthesis of 17-beta keto androstenones normally involve a Grignard reaction. For example, the 17-beta thiopyridyl ester (see reference J. Med. Chem., Vol. 29, No. 11, pp. 2298–2315 by Rasmusson, et al.) or the 17-beta imidazolide (see reference J. Med. Chem., Vol. 29, No. 11, pp. 2298–2315 by Rasmusson, et al.) can be reacted with suitable Grignard reagent to produce the 17-beta keto derivatives.

However, in general, these intermediates are very reactive, require special handling, and produce intermediates products which are difficult to purify.

Because of convenience and lower process costs, a common route used to make these materials is via a Grignard reaction in which an androstenone 17-beta carboxylic alkyl ester, e.g. methyl ester, which is more stable than the corresponding thiopyridyl ester or imidazolide, is reacted with a Grignard reagent, e.g. isobutylmagnesium bromide. However, the yields are modest, e.g. 30–60%, due to the fact that the desired product ketone reacts further with the Grignard reagent as it is formed to produce the undesired secondary and tertiary alcohols. This situation generally necessitates chromatographic separation of impurities formed in the process, e.g. the secondary and tertiary alcohols, which is not commercially practical on a large scale.

What is desired in the art is a more convenient, higher yielding process which does not involve time-consuming and costly purification procedures.

SUMMARY OF THE INVENTION

We have found that by conducting the standard Grignard reaction in the novel presence of hexamethyldisilazane (HMDS) good yields of 17-beta $C_3$–$C_{10}$ ketones of 3-oxo-4-aza-5-α-androst-1-enes can be produced.

By this invention there is provided a process for making a compound of the following formula:

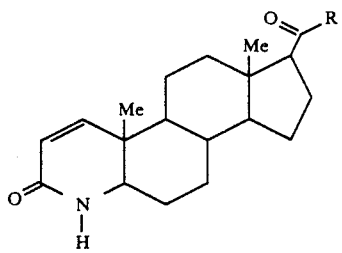

II comprising the step of contacting the compound of the formula:

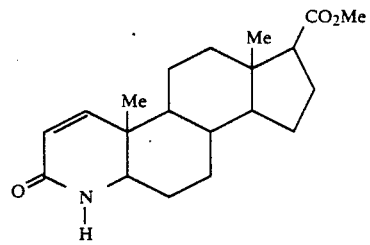

I with a Grignard reagent of the formula:

RMgX, wherein

R is $C_3$–$C_{10}$ linear or branched alkyl; and

X is iodine, bromine, or chlorine; in a dry inert organic solvent at a temperature in the range of $-5°$ to $65°$ C., in the presence of hexamethyldisilazane, for a sufficient time to form compound II.

BRIEF DESCRIPTION OF THE INVENTION AND PREFERRED EMBODIMENTS

The invention can be easily understood by reference to the following Scheme:

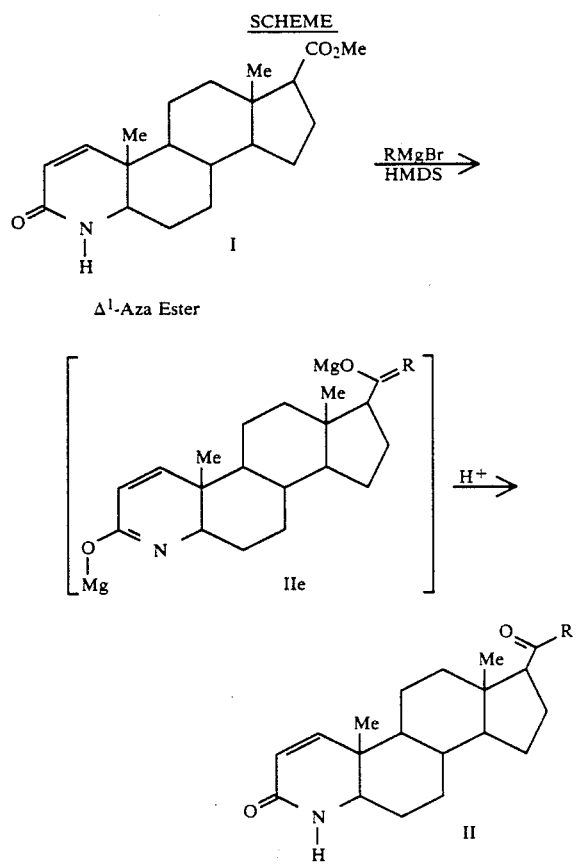

It is believed that the hexamethyldisilazane, as the magnesium amide base, promotes enolization of the initially formed ketone to form the intermediate IIe, thus inhibiting further reaction with the Grignard reagent to produce undesired secondary and tertiary alcohols.

The starting methyl ester I, referred to herein as "Δ¹-aza ester," is known and available by the procedure of Rasmusson, et al. U.S. Pat. No. 4,377,584, hereby incorporated by reference for this particular purpose.

The Grignard Reagent, RMgX, is available and can be prepared by standard methods in the art, e.g. by reacting RX with magnesium metal in anhydrous diethyl ether, tetrahydrofuran, dioxane, and the like.

The R radical is a $C_3$–$C_{10}$ linear or branched alkyl group, e.g. methyl, ethyl, isopropyl, isobutyl, sec-butyl, isopentyl, isohexyl, t-octyl, n-decyl and the like.

X is a halogen selected from bromine, chlorine or iodine.

Hexamethyldisilazane, $(CH_3)_3SiNHSi(CH_3)_3$, is commercially available. This reagent is used in a molar ratio of Δ¹-aza ester: Grignard Reagent: HMDS of about 1:3:10.

Generally, the Grignard reagent is made first by adding the magnesium to an anhydrous solvent, e.g. THF, at room temperature under an inert atmosphere, e.g. dry nitrogen, and then adding the $C_3$–$C_{10}$ alkyl halide to form the Grignard reagent.

The formed Grignard reagent is then added to a suspension of the Δ¹-aza ester and HMDS in the same dry solvent at about −5° to 65° C., preferably −5° to 10° C. with stirring and cooling.

Generally, the resulting solution is stirred at room temperature for about 1–2 hours then heated to reflux for 10–12 hours under an inert atmosphere.

Workup is conventional and involves quenching the reaction mixture into dilute aqueous acid, e.g. 2N HCl, followed by separation of the aqueous layer, and crystallization of the product out of the organic layer.

Yields in the process of the 17-beta branched alkyl ketone are in the range of 70 to 90%.

Solvents useful in the process include the standard Grignard solvents, e.g. $C_4$–$C_6$ linear, branched, or cyclic ethers, e.g. diethyl ether, tetrahydrofuran, dioxane, dimethoxyethane and the like.

The following examples are for illustrative purposes only, and should not be construed as being limitations on the scope or spirit of the instant invention.

EXAMPLE 1

Isobutylmagnesium Bromine

A three-neck 1 L flask equipped with an overhead stirrer, a nitrogen inlet, and a 125 mL addition funnel was charged with 12.0 g of magnesium metal and 225 mL of anhydrous THF.

To the mixture at 20° C. was added isobutyl bromide (initial charge: 5 mL, total charge: 49.3 mL, 0.450 mol). After an initiation period, the temperature rose to 40°–43° C. After the temperature had begun to subside, isobutyl bromide was added at a rate which maintained the temperature at 40°–43° C.

After the addition of the bromide was complete, the temperature was maintained at 40° C. for 12 hours before filtering at 40° C. through a medium sintered glass funnel to remove residual magnesium.

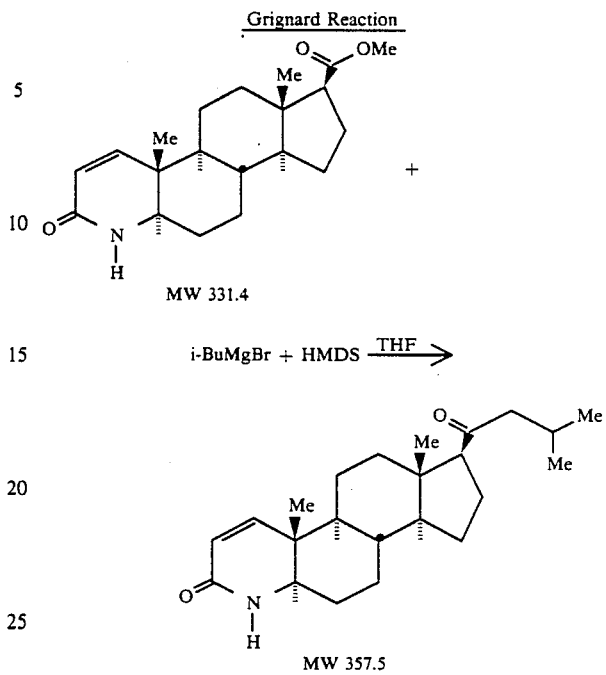

In a three-neck 1 L flask equipped with an overhead stirrer, a nitrogen inlet, and reflux condenser was placed 220 mL of anhydrous tetrahydrofuran and 10.0 g of Δ¹-aza ester (I). The system was evacuated and filled with nitrogen three times. Hexamethyldisilazane (HMDS) (19.1 mL, 90.6 mmol) was added and the slurry was cooled to −5° C.

A solution of isobutylmagnesium bromide in anhydrous tetrahydrofuran (232 mL, 1.30M) was added at a rate such that the internal temperature did not exceed 10° C.

The mixture was warmed to 20°–25° C. for 1 hour, heated at reflux for 12 hours, then cooled to 0° C. and quenched into cold (0° C.) 2N HCl (200 mL) maintaining the internal temperature below 20° C.

The mixture was warmed to 25° C. and stirred for 1 hour. After a one hour settling period, the layers were separated and the upper organic layer containing suspended product was concentrated to 100 mL by atmospheric distillation. After cooling to 20° C., the white crystalline product was isolated by filtration washing with 40 mL of THF and was suction dried for 4 hours to give 9.41 g (85.5% yield) of 23-methyl-4-aza-5-alpha-21-norchol-1-ene-3,20-dione, containing less then 0.5% of the corresponding secondary alcohols.

The crude product (5.20 g) was dissolved in acetic acid (208 mL) at 40° C.

The solution was filtered through a 10–20μ sintered glass funnel into a 1 L three-neck flask equipped with a mechanical stirrer, a vacuum/nitrogen adapter washing the funnel with two 10 mL portions of acetic acid. The temperature was maintained at 40° C. Water (400 mL) was added over 30 minutes and the resulting solution was allowed to cool to 20° C. and age overnight before filtering. The cake was washed with 30 mL of 50:50 acetic acid/water. After preliminary drying on the filter funnel, the solid was dried at 70°–80° C. (nitrogen sweep) for 36 hours to provide 4.99 g of the titled product in 84.4% yield overall from Δ¹-aza ester (I).

HPLC

Column: DuPont Zorbax Phenyl, 25 cm × 4.6 mm.

Solvent: 50% $H_2O$ (0.1% $H_3PO_4$, 1.0% $CH_3CN$), 50% $CH_3CN$.

Flow: 2 mL/min.

Wavelength: 210 nm.

Sample vol.: 10 μL.

Detector: LDC Spectro Monitor 1204A, AUFS=0.05

| RT: | $\Delta^1$-Aza ester (I) | 5.54 min |
|---|---|---|
| | Ketone II (R = iBu) | 10.27 min |
| | Secondary alcohols | 6.52 min |
| | | 7.52 min |
| | Tertiary alcohol | 26.08 min |

Analytical Controls

HPLC: area %=99.5.

TLC: 4 impurities each <0.5%.

Rotation: $[\alpha]_{405} = +164.1°$ C., (25° C., c=1, HOAc).

Color: 1.7 (c=1, HOAc).

Carrying out the above-described reaction in the absence of HMDS results in a yield of 78% by assay (cf. 93% with HMDS) and would necessitate time-consuming chromatographic steps during isolation and purification to remove the secondary, 5% (cf. 1% with HMDS) and tertiary, 15%, (cf. 3% with HMDS) alcohols formed.

What is claimed is:

1. A process for making a compound of the following formula:

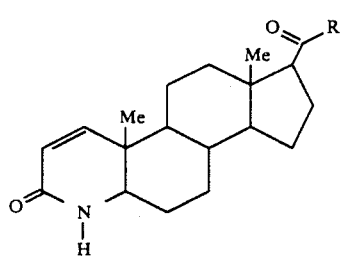

comprising the step of contacting the compound of the formula:

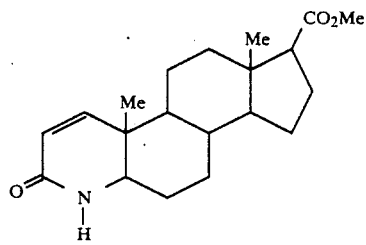

with a Grignard reagent of the formula:

RMgX, wherein

R is $C_3$–$C_{10}$ alkyl; and

X is iodine, bromine, or chlorine; in a dry inert organic solvent at a temperature in the range of −5° to 10° C., in the presence of hexamethyldisilazane, for a sufficient time to form Compound II where in the molar ratio of $\Delta^1$-azaester: Griganard reagent: HMDS of about 1:3:10.

2. The process of claim 1 wherein R is isobutyl.

3. The process of claim 1 wherein X is bromine.

4. The process of claim 1 wherein the solvent is a $C_4$–$C_6$ linear or branched cyclic ether.

5. A process for making a compound of the following formula:

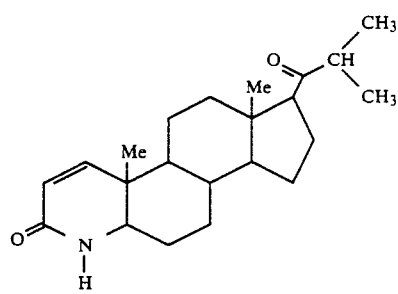

comprising the step of contacting the compound of the formula:

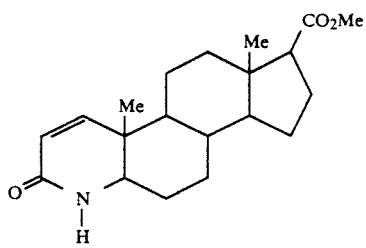

with a Grignard reagent of the formula:

RMgX, wherein

R is $C_3$ branched alkyl; and

X is iodine, bromine or chlorine; in a dry inert organic solvent at a temperature in the range of −5° to 10° C., in the presence of hexamethyldisilazane, for a sufficient time to form Compound 2 where in the molar ratio of $\Delta^1$-azaester: Grignard reagent: HMDS of about 1:3:10.

* * * * *